US006821959B1

(12) United States Patent
Anzaghi et al.

(10) Patent No.: US 6,821,959 B1
(45) Date of Patent: Nov. 23, 2004

(54) ANTIBIOTIC-NATURAL POLYSACCHARIDE POLYMER ADDUCTS

(75) Inventors: Piergiorgio Anzaghi, San Colombaro Al Lambro (IT); Rosanna Stefli, Pavia (IT)

(73) Assignee: Istituto Biochimico Pavese Pharma S.p.A, Pavia (IT)

( * ) Notice: Subject to any disclaimer, the term of this patent is extended or adjusted under 35 U.S.C. 154(b) by 0 days.

(21) Appl. No.: 09/979,240

(22) PCT Filed: May 16, 2000

(86) PCT No.: PCT/EP00/04374

§ 371 (c)(1),
(2), (4) Date: Nov. 19, 2001

(87) PCT Pub. No.: WO00/78287

PCT Pub. Date: Dec. 28, 2000

(30) Foreign Application Priority Data

May 18, 1999 (IT) .......................................... MI99A1085

(51) Int. Cl.⁷ ................................................ A61K 31/70
(52) U.S. Cl. ............................. 514/59; 514/35; 514/54; 514/58
(58) Field of Search ............................. 514/35, 54, 58, 514/59, 29, 33, 34, 36, 40

(56) References Cited

U.S. PATENT DOCUMENTS 4,315,002 A    2/1982  Maurer ........................ 424/181

FOREIGN PATENT DOCUMENTS

| EP | 0392487 | 10/1990 | .......... A61K/31/71 |
| EP | 0428486 | 5/1991 | .......... A61K/47/48 |
| EP | 0438747 | 7/1991 | .......... A61K/37/02 |
| WO | WO9737638 | 10/1997 | ............ A61K/9/14 |
| WO | WO9850018 | 11/1998 | ............ A61K/9/16 |

OTHER PUBLICATIONS

Molteni, "Effects of the Polysaccharidic Carrier on the Kinetic Fate of Drugs Linked to Dextran and Insulin in Macromolecular Compounds", Medea Research, Alfred Benzoo Symposium 17, Editors: Hera Boadgaard, Copenhagen (1982).

Grishin, G.I., Tr. Leningrad Khim. Farm. Inst. 27, 113–18 (1969).

Primary Examiner—Elli Peselev
(74) Attorney, Agent, or Firm—Abelman, Frayne & Schwab

(57) ABSTRACT

Antibiotic-natural polysaccharides polymer adducts based on non-covalent and non-ionic bonds, with an improved profile of activity compared with the corresponding antibiotic.

11 Claims, No Drawings

ANTIBIOTIC-NATURAL POLYSACCHARIDE POLYMER ADDUCTS

FIELD OF THE INVENTION

The present invention concerns antibiotic-natural polysaccharide polymer adducts based on non-covalent and non-ionic bonds, with an improved profile of activity compared with the corresponding antibiotic.

STATE OF THE ART

Many difficulties arising out of the chemotherapeutic treatment derive from the fact that some active principles do not possess optimum pharmacological and pharmaco-kinetic characteristics. One of the approaches used by the pharmaceutical technique to face the problems caused by a low bio-availability or a limited duration of the antibiotic effect, following oral or parenteral administration, consists in bonding the antibiotic to natural or synthetic, inert and biocompatible polymers. However, the tests conducted in the bonding sector with polymers have reached a limited and, in particular, scarcely foreseeable, success. Grishin G. I., Tr. Leningrad, Khim-Farm. Inst. (1969), 27, 113–18, describes the interaction between penicillins or tetracyclines and some natural polysaccharides of microbic origin. The result of these interactions is far from being quantifiable and qualifiable, since, in some cases, the interaction is absent or low, in other cases it actually exists but does not produce any effects on in the antibiotic activity. This may be ascribable to a variety of reasons, such as the nature of the bond and the relationship between the molecules.

The antibiotic-polymer associations that have proved to be successful concern classes of well-defined antibiotics or single antibiotics, and are often characterized by the formation of covalent or ionic-bond complexes or conjugates, The patent application EP 0 392 487 (in the name of Takeda Chemical Industries Ltd.) describes a complex consisting of an anthracyclinic antibiotic bearing an aminosaccharide residue and a polyanion described as a natural or synthetic polymer with negatively charged residues, capable of forming ionic bonds with the positively charged aminosaccharide residues. Compare with the antibiotic, this complex has better characteristics of stability with at neutral pH, and this allows the production of slow-dropout release preparations, free of irritating effects on tissues.

The EP 0 428 486 patent (in the mane of Sandoz Ltd.) claims a water-soluble polimixin conjugate with a carrier, e.g. a polysaccharide such as dextran, which has a higher half-life and power activity compared to native poliximin. This conjugate's bond is of the aminic or carbamate type, i.e. covalent.

Molteni L., Optimization of Drug Delivery, Alfred Benzon Symposium 17, publishers: Hera Bundgaard. Anne Bagger Hansen, Helmer Hafod, Munksgaard, Copenhagen, 1982, deals discusses with the interaction of various types of substances, among which some antibiotics and polysaccharides, e.g. dextrans or inulin. The interaction is clearly of the covalent type because, due to the low chemical reactivity of polysaccharides and the presence of a number of hydroxilylic groups, the interaction Is said to be based on ester bonds with substances possessing carboxylic groups, or the hydroxylic groups may be oxidized to aldehydes or be replaced with reactive groups.

The covalent/ionic bonded polymer-antibiotic conjugate does not provide sure dependable results and, moreover, it represents and expensive and complex approach, from the a regulatory standpoint, to the solution of the activity problems, mentioned above, because (being chemical entities based on strong bonds, such as the covalent and ionic bond) these conjugates, which are pro-drugs, are considered as new compounds and it is necessary to characterize them chemically, to study their pharmaco-dynamic profile and clinical effectiveness.

The patent application EP 0 438 747 (in the name of Shionogi Seiyaku Kabushiki Kausha) claims a stable freeze-dried product composed of a glycopeptidic antibiotic and a water-soluble saccharyde, such as a polysaccharide (e.g. dextran), which is used in low percentages and has the function of a support stabilizer during the freeze-drying process. The glycopeptidic antibiotics, such as vancomycin are very particular drugs, particularly complex from a chemical standpoint, not orally administerable and, in a few cases, such as vancomycin, not even intramuscularly. In some cases, they may be highly nephrotoxic.

A composition containing a pharmaceutical or diagnostic agent and dextran is disclosed by the U.S. Pat. No. 4,315,002. Said agent may be an antibiotic or an enxyme and the composition is particularly suitable for sensitive pharmaceutical active compounds and enzymes for diagnostic purposes and for biochemical analyses.

SUMMARY OF THE INVENTION

It has been now surprisingly found that antibiotic-natural polysaccharide adducts, characterized by weak bonds—such as, for example, the hydrogen bond—compared to the same free antibiotic, have an equal or higher microbiological activity or therapeutic effectiveness, with reduced molar doses of the antibiotic and, inter alia, are less toxic.

DESCRIPTION OF THE INVENTION

The object of the present invention is represented by antibiotic-natural polysaccharide adducts, in which the interaction between the two components is based on non-covalent and non-ionic bonds.

More specifically, the adducts of the present invention contain an antibiotic selected from the group consisting of β-lactam, aminoglycoside and macrolide antibiotics, linked by a non-covalent and non-ionic bond to a natural polysaccharide.

Among the preferred antibiotics preferred according to the present invention penicillins such as amoxicillin; cephalosporins such as cefadrin, axetilcefuroxime, cefazolin, cefotaxime and cefotriaxone; aminoglycosides such as neomycin, gentamicin, amikacin and apramicin; macrolides such as erythromycin, roxitromycin and azytromycin are cited. Amoxicillin, cefadrin and gentamicin are particularly preferred.

The polysaccharides useful for the present Invention are biocompatible and inert and, therefore, have no effects from a pharmacological and toxicological standpoint. They are possibly preferably selected among dextrans, inulin and maltodextrin. For the purposes of the present invention, a special preference is given to dextrans.

Dextrans are hydrophilic and water-soluble polymers, stable to against the enzymatic attack, consisting of linear chains of (-D glucose molecules. Their molecular weight ranges from 1,000 Dalton (dextran 1) to 110,000 Dalton (dextran 110). Dextrans having a molecular weight below 4,000 Dalton, are completely excreted eliminated in the urine within 48 hours, while those having higher molecular weights remain in circulation for longer periods. For the uses of the present invention, the preference is given to dextrans 4–70, i.e. having a molecular weight ranging from 4,000 to 70,000 Dalton.

According to the present invention, the antibiotic percentage over the total adduct may range from 20% to 60% by weight.

The bond between the antibiotic and the polysaccharide in the adduct of the present invention is of the non-covalent and non-ionic type, as may be easily deduced from the mode of preparation of these adducts, requiring a co-solution in water of the polysaccharide and the antibiotic and the remotion of the solvent by known thecniques such as lyophilization and spray drying. This allows the hydrophilic interaction between the OH groups, either carboxylic or not, of the antibiotic and those of the polysaccharide, through weak bonds so called just because they need for less energy (approx. 3–5 kcal/mol.) to be crackedbroken, compared to covalent and ionic bonds, which require an energy of at least 50–100 kcal/mol. As shown In Remington's Pharmaceutical Science, XVIII ed., page 186 seq., where these adducts are named "molecular complexes", the kind of interaction may be of various type (from the hydrogen bond to the hydrophobic interaction to the charge transfer).

The adducts of the present invention are obtained through quick and economical processes, compared to the traditional approaches that use a covalent bond between the antibiotic and the polysaccharide carrier and therefore they constitute products having now characteristics.

Therefore, another objective of the present invention consists in the process necessary for preparing antibiotic-natural polysaccharide adducts comprising the dissolution of the two adduct components in distilled water, so as to obtain a limpid solution, the tittering and the isolation of the adduct from the solvent through adequate techniques.

The process of the present invention may optionally require the presence, during the dissolution phase, of solubilising and buffer agents and preservatives.

In the case of injectable preparations, the distilled water used in the process of the present invention is depyrogenated and sterile water for injectable use; moreover, the solution is sterilized through 0.1 to 0.45 $\mu$m (preferably 0.2 $\mu$m) filters and divided among depyrogenated and sterilized vials, operating under a laminar flow hood, in a sterile ambient.

Preferably, the technological processes used for the isolation of the adduct from the solution are freeze drying and nebulization (spray drying), that to allow the yielding of a product in an physical form optimal for the subsequent formulation.

The adduct obtained through a the nebulization process is a light, white, water-soluble powder, especially fit for the preparation of oral formulations administrations (tablets, capsules, granules). The freeze-dried product, particularly suitable for injectable preparations, has a compact and whitish appearance and, if previously depyrogenated and sterilized, immediately restore the limpid solution of the physiologic-pH adduct through the addition of water for injectable applications.

Considering the observations made above, a further aspect of the present invention concerns the compositions prepared by freeze drying or spray drying of natural antibiotic-polysaccharide adducts described above.

The formation of these adducts favourably modifies some of the pharmacological pharmaco-kinetic characteristics of the antibiotic. In fact the adducts with low molecular weight polysaccharides can increase the solubility of a low soluble antibiotic and, then, its bio-availability when administered by oral route. In case of injection therapy, the us of a high molecular weight polysaccharide allows the extension of the circulation time and, consequently, prolongs its effect.

The adduct activity has been measured in vitro using the methods explained below, in examples 5 and 6, and in vivo, by administering rats infected by a strain sensitive to the antibiotic in question (examples 7 and 8).

The present invention also comprises includes the use of antibiotic-natural polysaccharide adducts based on non-covalent and non-ionic bonds, for the treatment of pathologies in humans and animals.

Examples of implementation of the present invention are provided below.

EXAMPLE 1

Synthesis of the Amoxicillin-dextran 40 Adduct

Dextran 40 (40,000 Dalton) (4 g) and amoxicillin tryhydrate(7.15 g, equal to 6 g of base; title: 100%, solubility: 3.3 m/ml of water, pH=5) were dissolved in distilled water (2 l), with sodium bicarbonate to pH around 7. The adduct solution (60% by weight of amoxicillin) was sprayed with a mini spray-dryer (Mini Buchi), at a jet pressure of 800 mbar, an inlet temperature of 130° C., an outlet temperature of 50° C. and a total suction of 100%. The recovered product (adduct yield: 98%) was placed in hermetically sealed containers.

Amoxicillin title in the adduct: 58.98% by weight (HPLC); pH: 7.6. Water solubility 9 mg/ml.

EXAMPLE 2

Synthesis of the Cefradine-dextran 5 Adduct

Dextran 5 (5000 D) (96 g) and cefradine (26.23 g, title: 100%, solubility: 4 mg/ml of water, pH=4.8) were dissolve in distilled water (1.75 l) and this solution was poured onto freeze spraying drying trays. The freeze drying cycle has required the following temperatures: −40° C. for the pre-freezing, −10° C. during the freeze drying, +10° C. for drying and +35° C. for the secondary drying. A vacuum of $2.2 \cdot 10^{-2}$ mbar was maintained. The obtained product (adduct yield by weight: 99%) was a soft, impalpable and whitish powder, quickly soluble in a water solvent (13 mg/ml).

Cefradine title in the adduct: 20% by weight (HPLC); pH: 4.5

EXAMPLE 3

Synthesis of the Cefazolin-inulin Adduct

Inulin (8.17 g) was dissolved under magnetic stirring in distilled water for injectables (40.5 ml), alternatively adding anhydrous cefazolin (12.27 g; title: 100%, pH=3.2) and sodium bicarbonate to pH=6.5. The resulting solution (60% of cefazolin by weight) was tittered using a 0.2 $\mu$m sterilizing filter, divided among depyrogenated and sterilized vials positioned in a freeze sprayer dryer programmed to run a cycle like the one indicated in Example 2. The product obtained (adduct yield: 98.7%) had the following characteristics:

Cefazolin title in the adduct: 58.30% by weight (HPLC); pH: 5.5

EXAMPLE 4

Synthesis of the Gentamicin-dextran 70

Sodium methyl-p-hydroxybenzoate (1.8 g) was dissolved in boiling distilled water for injectables (200 ml), then added with sodium propyl-p-hydroxybenzoate (0.2 g) and EDTA (0.1 g), bringing the solution to room temperature and to 800 ml. Then, sodium metabisulfite (3.2 g) and gentamicin base (20 g; title: 100%) were added, followed by dextran 70 (20 g), under during stirring, and other distilled water, until a volume of 1 l. The injectable solution containing 50% gentamicin by weight was filtered using a sterile filter, divided among various depyrogenated and sterilized vials under a laminar flow hood and lyophilized.
Gentamicin title in the adduct: 50% by weight (diffusion titration);
pH: 3.2

EXAMPLE 5

Determination of the Inhibition Halos

The inhibition halos were obtained through the diffusion method (Farmacopea Ufftclale Italiana, IX ed., page 315), using a culture medium "Mueller-Hinton Medium Difco, with a low thymine and thymidine content, in sterile Petri plates (9 cm in diameter), with Tryptic Soy Broth (Difco).

For the sensitivity test, both paper filtering disks, imbibed of a fixed quantity of antibiotic and the relevant adduct disks, having the same total dose, but a lower molar ratio of the active principle were prepared.

To produce a bacterial growth, a strain of *Staphylococcus aureus* ATCC 6538 P (strain A) and two strains of field Staphylococcus aureus (strains B and C) were used.

The culture broths were prepared placing a loop of bacterial coating of an agar culture (12 h) in a test tube containing sterile Tryptic Soy Broth (5 ml), successively incubated at 37° C. for 4 hours.

When necessary, the suspensions have been diluted with sterile water in order to obtain a turbidity similar to the reference standard (0.5 McFarland). The Mueller-Hinton culture medium (150 ml) was sterilized at 121° C. for 15 minutes; a part of it was positioned on sterile Petri plates (9 cm in diameter), was let to solidify, while another part was cooled at approx. 45° C., was inoculated with the bacterial suspensions as above prepared (15 ml) and poured onto the solidified agar surface (10 ml per plate).

The sown plates were let dry (open) under a laminar flow hood for 15 minutes, then the disks were placed on their surface (four each plate), i.e. the adduct and antibiotic according to the two desired concentrations. The prepared plates (five each tests) were overturned and incubated at 37° C. for 16 hours. After this interval, the inhibition halos were produced. The results are shown in Table 1, where F.U. indicates the dosage recommended by Farmacopea Ufficiale Italiana, IX ed., vol. 1

TABLE 1

| Antibiotic | Adduct | Dose ($\mu$g) | Halos (mm) antibiotic on strain | | | Halos (mm) adduct on strain | | |
|---|---|---|---|---|---|---|---|---|
| | | | A | B | C | A | B | C |
| Amoxy-cillin | Example 1 | 4 | 12.0 | 13.0 | 9.7 | 11.3 | 12.7 | 10.0 |
| | | 8 | 13.2 | 14.0 | 10.0 | 13.0 | 13.7 | 10.3 |
| Cefradin | Example 2 | 0.64 (F.U.) | 10.0 | 7.0 | 9.7 | 9.0 | 5.9 | 8.5 |
| | | 1.56 (F.U.) | 12.1 | 9.0 | 10.0 | 11.2 | 8.5 | 10.0 |
| Cefazolin | Example 3 | 0.64 (F.U.) | 11.0 | 8.5 | 10.1 | 9.9 | 8.0 | 8.7 |
| | | 1.56 (F.U.) | 12.2 | 10.1 | 10.9 | 11.2 | 11.0 | 10.0 |
| Genta-micin | Example 4 | 4 | 12.1 | 11.8 | 12.8 | 11.6 | 11.0 | 12.6 |
| | | 6 | 13.1 | 12.0 | 13.9 | 12.9 | 11.6 | 13.0 |

EXAMPLE 6

Determination of the Minimum Inhibiting Concentration (MIC) In vitro

The minimum Inhibiting concentration values were determined through the method of dilutions in a liquid medium, using a Mueller-Hinton broth with a pH=7.4, sterilized at 120° C. for 20 minutes. Scalar concentrations were added to a series of test tubes containing a fixed volume of culture medium, to double the antibiotic or adduct, from 0.4 (g/ml to 50 (g/ml, apart from amoxicillin, as its values ranged from 0.02 U.O./ml to 4.8 U.O./ml (corresponding to 0.012–2.88 (g/ml).

A drop of broth (dilution 1:10) was added to all test tubes, which were incubated at 37° C. for 18–24 hours. Then, the test tube with the highest dilution free of any turbidity was considered as the one containing the minimum inhibiting concentration (MIC). The results are shown in Table 2.

TABLE 2

| Antibiotic | Adduct | MIC ($\mu$g/ml) of antibiotic on strain | | | MIC ($\mu$g/ml) of adduct on strain | | |
|---|---|---|---|---|---|---|---|
| | | A | B | C | A | B | C |
| Amoxycillin | Example 1 | 0.1 | 0.2 | 0.08 | 0.138 | 0.25 | 0.06 |
| Cefradin | Example 2 | 4.0 | 4.8 | 4.3 | 5.1 | 5.9 | 6.3 |
| Cefazolin | Example 3 | 0.5 | 0.64 | 0.54 | 0.9 | 0.68 | 0.7 |
| Gentamicin | Example 4 | 0.125 | 0.15 | 0.139 | 0.13 | 0.156 | 0.14 |

EXAMPLE 7

In vivo Activity

The antibiotics and the respective adducts were used in solution with distilled water for injectables or with purified water for oral use. Common albino mice (average weight: 28 g), previously infected with *Staphylococcus aureus* (which is not resistant to the examined antibiotics), that had developed ulcerative dermatitis, with localized abscesses and popodermatitis (mastitis) were treated with the prepared solutions every 24 hours for 5 days. After this treatment, a bacteriologic checking through isolation was performed, using pads on the animal skin and inoculating the sample drawn from the rat on the plate. The results are shown in tables 3 to 6 below.

TABLE 3

| Compound | No. of infected subjects | Post-infective clinical symptoms | Bacteriologic test after 5 days of therapy | | % of recovery |
|---|---|---|---|---|---|
| | | | positive | negative | |
| Amoxycillin | 13 | YES | 0 | 13 | 100 |
| | 2 | NO | 0 | 0 | |
| Adduct of Example 1 | 14 | YES | 2 | 12 | 85 |
| | 1 | NO | 0 | 0 | |
| Infected controls | 15 | YES | 15 | 0 | |
| Uninfected controls | 15 | NO | | | |

TABLE 4

| Compound | No. of infected subjects | Post-infective clinical symptoms | Bacteriologic test after 5 days of therapy | | % of recovery |
|---|---|---|---|---|---|
| | | | positive | negative | |
| Cefradin | 15 | YES | 0 | 15 | 100 |
| Adduct of Example 2 | 14 | YES | 2 | 12 | 85.7 |
| | 1 | NO | 0 | 0 | |

TABLE 4-continued

| Compound | No. of infected subjects | Post-infective clinical symptoms | Bacteriologic test after 5 days of therapy positive | Bacteriologic test after 5 days of therapy negative | % of recovery |
|---|---|---|---|---|---|
| Infected controls | 15 | YES | 15 | 0 | |
| Uninfected controls | 15 | NO | | | |

TABLE 5

| Compound | No. of infected subjects | Post-infective clinical symptoms | Bacteriologic test after 5 days of therapy positive | Bacteriologic test after 5 days of therapy negative | % of recovery |
|---|---|---|---|---|---|
| Cefazolin | 15 | YES | 0 | 15 | 100 |
| Adduct of Example 3 | 13 | YES | 2 | 11 | 84.6 |
| | 2 | NO | 0 | 0 | |
| Infected controls | 15 | YES | 15 | 0 | |
| Uninfected controls | 15 | NO | | | |

TABLE 6

| Compound | No. of infected subjects | Post-infective clinical symptoms | Bacteriologic test after 5 days of therapy positive | Bacteriologic test after 5 days of therapy negative | % of recovery |
|---|---|---|---|---|---|
| Gentamicin | 13 | YES | 0 | 13 | 100 |
| | 2 | NO | 0 | 0 | |
| Adduct of Example 4 | 14 | YES | 2 | 12 | 85 |
| | 1 | | 0 | 0 | |
| Infected controls | 15 | YES | 15 | 0 | |
| Uninfected controls | 15 | NO | | | |

EXAMPLE 8

Efficacy Study of Three Cephalosporins and their Respective Adducts in a Murine Model of *Staphylococcus aureus* Abscess The efficacy of three conventional cephalosporins and their respective adducts with only 60% of drug in the therapy of a murine model of *Staphylococcus aureus* subcutaneous abscess is described.

The test articles were:
Ceftriaxone 25 mg
Ceftriaxone 15 mg+10 mg dextran5 (freeze-dried adduct)
Cefotaxime 25 mg
Cefotaxime 15 mg+10 mg dextran5 (freeze-dried adduct)
Cefazoline 25 mg
Cefazoline 15 mg+10 mg dextran5 (freeze-dried adduct)

200 Male swiss mice were housed in temperature and humidity controlled animal rooms. The body weight on the day of infection was 25 g (SD 1.2, no 10).

Culture media Brain Heart Infusion Broth (Difco) (BHI) and Brain Heart Infusion Agar (Merck) (BHIA) were prepared according to the manufacturer instructions and autoclaved for 15 mins at 121° C.

*S. aureus* Smith BT13 was used at infecting organism. It was stored frozen at −80° C.

The infective suspension was grown overnight on BHI at 36° C.±1° C. and diluted with BHIA in the ratio 5:1 so as to obtain an agar concentration of 2.5% in the infective suspension.

For each test article, a stock solution was prepared by dissolving the drug with 5 ml of water for injectables (5 mg/ml drug concentration for cephalosporins and 3 mg/ml for the adducts). Dilutions 1:2 and 1:4 were prepared using the same vehicles. All solutions were prepared immediately before use.

190 animals were infected subcutaneously with 0.3 ml of the bacterial suspension, whereas a negative control group of 10 mica was inoculated sc with 0.3 ml of sterile medium used for the bacterial suspension and not infected.

At 6 h after inoculation, groups of 10 mice were dosed intraperitoneally with 0.5 ml either of one of the antibiotic solutions, while an untreated control group of 10 mice was injected intraperitoneally with 0.5 ml sterile water.

On the two consecutive days, mice were dosed twice, For each conventional cephalosporin, tested doses were 100, 50 or 25 mg/kg/dose, whereas for the adducts 60, 30 or 15 mg/kg/dose.

On the third day after infection, all mice were sacrificed and autopsied. Presence and size of abscesses were recorded. The size was scored from 0 (no abscess) to 3 (approximately 1.5 cm$^2$). The activity of all compounds was compared by the non parametric Mann-Whitney U test. Statistical significance was for $p<0.05$.

Data on the presence and size of abscesses per treatment group are reported in Table 7.

For Ceftriaxone, the adduct was effective in curing 16/30 infected mice as compared with 11/30 for the parent compound. The total score was 34 for the derivative and 41 for the parent compound.

For Cefotaxime, the adduct as well as the parent compound cured 24/30 infected mice. Total score was 14 for both derivative and parent compound.

For Cefazolin, the adduct and the parent compound were similarly effective in the therapy of subcutaneous abscesses with 22 cured mice over the 30 infected. Total score was 22 for the derivative and 21 for the parent compound.

The polymer adducts of this invention containing 60% of Cefotaxime or Cefazoline and 40% of dextran5 have comparable efficacy to 100% dosage of the same cephalosporins against subcutaneous *S. aureus* infection in mice, while Ceftriaxone adduct appears to be more active in comparison with his parent drug.

TABLE 7

Number of mice with abscesses: treatment groups and total score

| Drugs | Doses (mg/kg) | | | | |
|---|---|---|---|---|---|
| Cephalosphorins | 0 | 25 | 50 | 100 | |
| Adducts | 0 | 15 | 30 | 60 | |
| Control (blank) Size scored | 0/10 0 | | | | Total abscesses in 30 mice |
| Control (infected) Size scored | 0/10 0 | | | | |
| Ceftriaxone Size scored | | 7/abcs/10 17 | 6/abcs/10 14 | 6/abcs/10 10 | 19 absc 41 |
| Ceftriaxone adduct Size scored | | 6/abcs/10 16 | 4/abcs/10 10 | 4/abcs/10 8 | 14 absc 34 |
| Cefotaxime Size scored | | 4/abcs/10 11 | 2/abcs/10 3 | 0/abcs/10 0 | 6 absc 14 |

TABLE 7-continued

Number of mice with abscesses: treatment groups and total score

| Drugs | Doses (mg/kg) | | | |
| --- | --- | --- | --- | --- |
| Cephalosphorins | 0 | 25 | 50 | 100 |
| Adducts | 0 | 15 | 30 | 60 |
| Control (blank) | 0/10 | | | |
| Size scored | 0 | | | |
| Control (infected) | 0/10 | | | Total abscesses in 30 mice |
| Size scored | 0 | | | |
| Cefotaxime adduct | | 4/abcs/10 | 2/abcs/10 | 0/abcs/10 | 6 absc |
| Size scored | | 10 | 4 | 0 | 14 |
| Cefazolin | | 6/abcs/10 | 2/abcs/10 | 0/abcs/10 | 8 absc |
| Size scored | | 17 | 4 | 0 | 21 |
| Cefazolin adduct | | 6/abcs/10 | 2/abcs/10 | 0/abcs/10 | 8 absc |
| Size scored | | 17 | 5 | 0 | 22 |

Taking into account the results described above, it seems clear that the adducts of the present invention—considering the antibiotic percentage contained therein—show an activity equal to or higher than the activity of the pure antibiotic. This is not ascribable to a synergy between antibiotic and polysaccharide in terms of pharmacological activity, since the polysaccharide is pharmacologically inert, but to the influence of the latter on the activity of the active principle.

What is claimed is:

1. A pharmaceutical formulation containing as an active ingredient a therapeutically effective amount of an adduct containing 20–60% in weight of an antibiotic selected from the group consisting of amoxicillin, gentamicin, cefriazone, cefradin, cefotaxime and cefazolin, linked to a natural polysaccharide by a non-covalent and non-ionic bond in combination with suitable excipients and diluents, wherein the therapeutic effective amount of said adduct is equal or lower than that of the antibiotic contained in a corresponding formulation containing as the active ingredient the antibiotic alone.

2. The pharmaceutical formulation according to claim 1, wherein the polysaccharide is selected from the group consisting of dextrans, inulin and maltodextrine.

3. The pharmaceutical formulation according to claim 1, wherein the polysaccharide is a dextran.

4. The pharmaceutical formulation according to claim 3, wherein the dextran has a molecular weight ranging from 1000 Dalton to 110000 Dalton.

5. The pharmaceutical formulation according to claim 3, wherein the dextran has a molecular weight ranging from 4000 to 70000 Dalton.

6. The pharmaceutical formulation according to claim 1 selected from the group consisting of tablets, capsules, granules and injectable preparations.

7. A therapeutic method for the treatment of a pathology caused by a bacterium comprising administrating to a human or animal in need thereof a therapeutically effective amount of at least one adduct containing 20–60% in weight of an antibiotic selected from the group consisting of amoxicillin, gentamicin, ceftriazone, cefradin, cefotaxime and cefazolin, linked to a natural polysaccharide by a non-covalent and non-ionic bond, wherein the therapeutically effective amount of said adduct is equal or lower than that of the antibiotic.

8. The therapeutic method according to claim 7, wherein the polysaccharide is selected from the group consisting of dextrans, inulin and maltodextrine.

9. The therapeutic method according to claim 8, wherein the polysaccharide is a dextran.

10. The therapeutic method according to claim 8, wherein the polysaccharide is a dextran having a molecular weight from 1000 Dalton to 110000 Dalton.

11. The therapeutic method according to claim 7, wherein the polysaccharide is a dextran having a molecular weight ranging from 4000 to 70000 Dalton.

* * * * *